United States Patent
Lohse et al.

(10) Patent No.: US 7,534,890 B2
(45) Date of Patent: May 19, 2009

(54) PROCESS FOR PREPARING 5-[(R)-2-(5,6-DIETHYL-INDAN-2-YLAMINO)-1-HYDROXY-ETHYL]-8-HYDROXY-(1H)-QUINOLIN-2-ONE SALT, USEFUL AS AN ANDRENOCEPTOR AGONIST

(75) Inventors: Olivier Lohse, Rixheim (FR); Caspar Vogel, Binningen (CH)

(73) Assignee: Novartis AG, Basel (CH)

( * ) Notice: Subject to any disclaimer, the term of this patent is extended or adjusted under 35 U.S.C. 154(b) by 520 days.

(21) Appl. No.: 10/546,941

(22) PCT Filed: Feb. 27, 2004

(86) PCT No.: PCT/EP2004/001981

§ 371 (c)(1),
(2), (4) Date: Aug. 25, 2005

(87) PCT Pub. No.: WO2004/076422

PCT Pub. Date: Sep. 10, 2004

(65) Prior Publication Data

US 2006/0252794 A1    Nov. 9, 2006

Related U.S. Application Data

(60) Provisional application No. 60/450,945, filed on Feb. 28, 2003.

(51) Int. Cl.
*C07D 215/02*    (2006.01)

(52) U.S. Cl. .......... 546/167; 546/153; 546/159
(58) Field of Classification Search .......... 546/153, 546/159, 167
See application file for complete search history.

(56) References Cited

FOREIGN PATENT DOCUMENTS

| WO | WO 95/25104 | * | 9/1995 |
| WO | WO9525104 | | 9/1995 |
| WO | 00/75114 | | 12/2000 |

OTHER PUBLICATIONS

Amlaiky et al., "Oxime ether derivatives with a carbostyril nucleus. 4. Synthesis and beta-blocking activity," Institute of Pharmacology and Experimental Medicine (ERA S42 du C.N.R.S., V. 206 de l'Inserm), 11 rue Humann 67000 Strasbourg, France (1984) (English translation).

* cited by examiner

*Primary Examiner*—D. Margaret Seaman
(74) *Attorney, Agent, or Firm*—Milagros Cepeda; Gregory Houghton

(57) ABSTRACT

A process for preparing 5-[(R)-2-(5,6-diethyl-indan-2-ylamino)-1-hydroxy-ethyl]-8- hydroxy-(1H)-quinolin-2-one salt. The process involves forming an acid salt of 5-[(R)-2-(5,6-diethyl-indan-2-ylamino)-1-hydroxy-ethyl]-8-substituted oxy-(1H)-quinolin-2-one; and converting the acid salt to a salt of 5-[(R)-2-(5,6-diethyl-indan-2-ylamino)-1-hydroxy-ethyl]-8-hydroxy-(1H)-quinolin-2-one without isolating the free base of 5-[(R)-2-(5,6-diethyl-indan-2-ylamino)-1-hydroxy-ethyl]-8-hydroxy-(1H)-quinolin-2-one.

22 Claims, No Drawings

PROCESS FOR PREPARING 5-[(R)-2-(5,6-DIETHYL-INDAN-2-YLAMINO)-1-HYDROXY-ETHYL]-8-HYDROXY-(1H)-QUINOLIN-2-ONE SALT, USEFUL AS AN ANDRENOCEPTOR AGONIST

This application claims benefit of U.S. Provisional Application No.60/450,945, filed Feb. 28,2003, which in its entirety is herein incorporated by reference.

The present invention provides a process for preparing 5-[(R)-2-(5,6-diethyl-indan-2-ylamino) -1-hydroxy-ethyl]-8-hydroxy-(1H)-quinolin-2-one salt without isolating the free base thereof which is unstable in organic solvents.

5-[(R)-2-(5,6-diethyl-indan-2-ylamino)-1-hydroxy-ethyl]-8-hydroxy-(1H) -quinolinone-2-one salts are β-selective adrenoceptor agonists with potent bronchodilator activity. For example, 5-[(R)-2-(5,6-diethyl-indan-2-ylamino)-1-hydroxy-ethyl]-8-hydroxy-(1H)-quinolinone-2-one maleate is especially useful for treating asthma and COPD. In addition, the maleate salt has been shown to have a very long duration of action in vitro and in vivo.

In a process for preparing 5-[(R)-2-(5,6-diethyl-indan-2-ylamino)-1-hydroxy-ethyl]-8-hydroxy-(1H)-quinolinone-2-one maleate, an epoxide, such as 8-substituted oxy-5-(R)-oxiranyl-(1H)-quinolin-2-one [Formula (I)], is reacted with an amine, such as 2-amino-(5-6-diethyl)-indan, to form a desired intermediate 5-[(R)-2-(5,6-diethyl-indan-2-ylamino)-1-hydroxy-ethyl]-8-substituted oxy-(1H)-quinolin-2-one [Formula (II)]. However, the reaction is not regioselective and delivers various amounts of a regioisomer [Formula (III)] and a dimer [Formula (IV)].

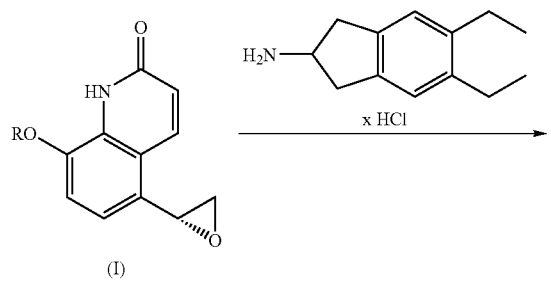

Generally, the reaction mixture above contains only about 60% to 80% of the desired intermediate having Formula (II). In addition, it is difficult to purify the intermediate having Formula (II) by crystallization without a high loss of yield. For example, silica gel chromatography has been used for such a purification, however, scale-up of silica gel chromatography is tedious and requires large volumes of solvents.

It would be desirable to develop a more efficient process for preparing 5-[(R)-2-(5,6-diethyl-indan-2-ylamino)-1-hydroxy-ethyl]-8-hydroxy-(1H)-quinolinone-2-one salts especially for large scale production, which provides the salts in high enantiomeric purity and high yield.

The invention provides a process for preparing 5-[(R)-2-(5,6-diethyl-indan-2-ylamino)-1-hydroxy-ethyl]-8-hydroxy-(1H)-quinolin-2-one salt or an acceptable solvate thereof comprising:

(i) reacting 8-substituted oxy-5-(R)-oxiranyl-(1H)-quinolin-2-one having Formula (I)

with 2-amino-(5-6-diethyl)-indan to form a reaction mixture containing compounds having Formulae (II), (III) and (IV)

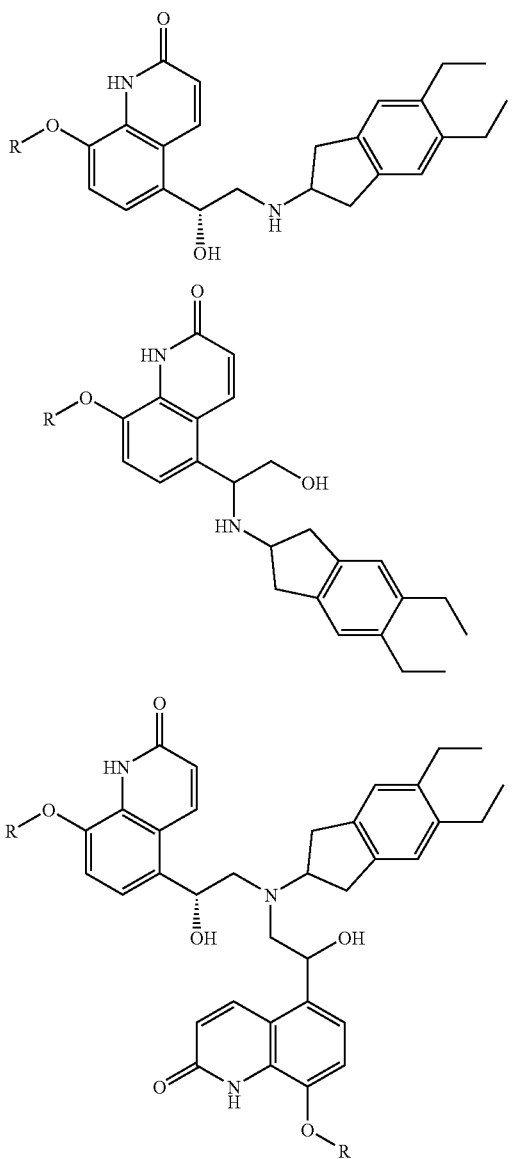

wherein R is a protecting group;

(ii) treating the reaction mixture prepared in Step (i) with an acid in the presence of a solvent to form a corresponding salt;

(iii) isolating and crystallizing a salt having Formula (V)

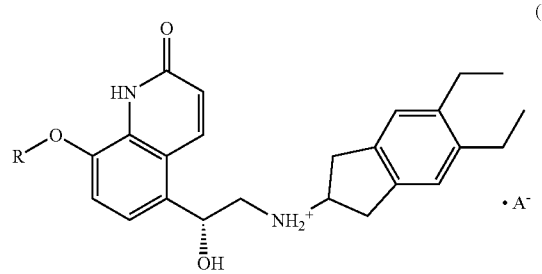

wherein R is a protecting group and A- is an anion;

(iv) removing the protecting group from the salt having Formula (V) in the presence of a solvent to form a salt having Formula (VI):

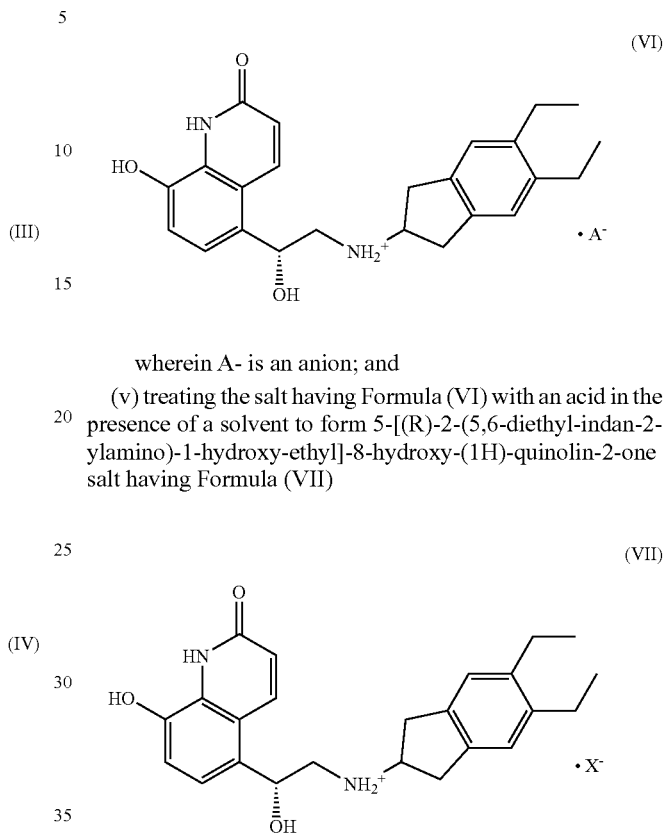

wherein A- is an anion; and (v) treating the salt having Formula (VI) with an acid in the presence of a solvent to form 5-[(R)-2-(5,6-diethyl-indan-2-ylamino)-1-hydroxy-ethyl]-8-hydroxy-(1H)-quinolin-2-one salt having Formula (VII)

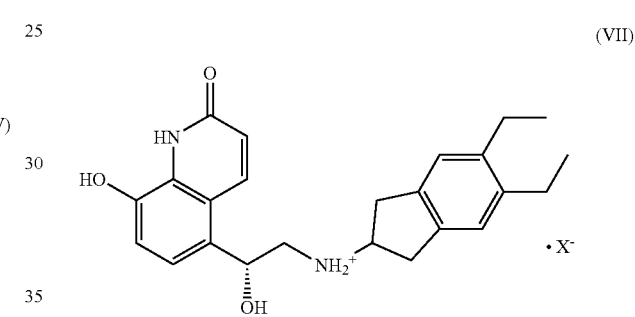

wherein X— is an anion.

Terms used in the specification have the following meanings:

As used herein, "alkyl" means straight chain or branched alkyl, which may be, e.g., $C_1$-$C_{10}$alkyl, such as methyl, ethyl, n-propyl, isopropyl, n-butyl, isobutyl, sec-butyl, tert-butyl, straight- or branched-pentyl, straight- or branched-hexyl, straight- or branched-heptyl, straight- or branched-nonyl or straight- or branched-decyl. Preferably alkyl is $C_1$-$C_4$alkyl.

"Aryl" means $C_6$-$C_{14}$aryl, preferably $C_6$-$C_{10}$aryl, and may be, e.g., substituted by at least one group selected from mercapto, dialkylamino, nitro, alkoxy, halogen, keto, cyano or a combination. Preferably aryl is phenyl.

"Alkoxy" means straight chain or branched alkoxy and may be, e.g., $C_1$-$C_{10}$alkoxy, such as methoxy, ethoxy, n-propoxy, isopropoxy, n-butoxy, isobutoxy, sec-butoxy, tert-butoxy or straight- or branched-pentoxy, -hexyloxy, -heptyloxy, -octyloxy, -nonyloxy or -decyloxy. Preferably alkoxy is $C_1$-$C_4$alkoxy.

"Alkenyl" means straight chain or branched-alkenyl, which may be, e.g., $C_2$-$C_{10}$alkenyl, such as vinyl, 1-propenyl, 2-propenyl, 1-butenyl, isobutenyl, or straight- or branched-pentenyl, -hexenyl, -heptenyl, -octenyl, -nonenyl or -decenyl. Preferred alkenyl is $C_2$-$C_4$alkenyl. "Cycloalkyl" means $C_3$-$C_{10}$cycloalkyl having 3- to 8-ring carbon atoms and may be, e.g., cyclopropyl, cyclobutyl, cyclopentyl, cyclohexyl, cycloheptyl or cyclooctyl, any of which can be substituted by one, two or more $C_1$-$C_4$alkyl groups, particularly methyl groups. Preferably, cycloalkyl is $C_3$-$C_6$cycloalkyl.

"Benzocycloalkyl" means cycloalkyl, e.g., one of the $C_3$-$C_{10}$cycloalkyl groups mentioned hereinbefore, attached at two adjacent carbon atoms to a benzene ring. Preferably, benzocycloalkyl is benzo-$C_5$-$C_6$cycloalkyl, especially, benzocyclohexyl (tetrahydronaphthyl).

"Cycloalkylalkyl" means $C_3$-$C_{10}$cycloalkyl$C_1$-$C_{10}$alkyl, where the $C_3$-$C_{10}$cycloalkyl group has 3- to 8-ring carbon atoms and may be, e.g., one of the $C_1$-$C_{10}$alkyl groups mentioned hereinbefore, particularly one of the $C_1$-$C_4$alkyl groups, substituted by one of the $C_3$-$C_{10}$cycloalkyl groups mentioned hereinbefore. Preferably cycloalkylalkyl is $C_3$-$C_6$cycloalkyl$C_1$-$C_4$alkyl.

"Aralkyl" means straight-chain or branched-$C_6$-$C_{10}$aryl$C_1$-$C_{10}$alkyl and may be, e.g., one of the $C_1$-$C_{10}$alkyl groups mentioned hereinbefore, particularly one of the $C_1$-$C_4$alkyl groups, substituted by phenyl, tolyl, xylyl or naphthyl. Preferably, aralkyl is phenyl$C_1$-$C_4$alkyl, particularly benzyl or 2-phenylethyl.

"Heterocyclic" means a monovalent heterocyclic group having up to 20 carbon atoms and one, two, three or four heteroatoms selected from nitrogen, oxygen and sulfur, the group optionally having an alkyl, alkylcarbonyl, hydroxyalkyl, alkoxyalkyl or aralkyl group attached to a ring carbon or nitrogen atom and being linked to the remainder of the molecule through a ring carbon atom, and may be, e.g., a group, preferably a monocyclic group, with one nitrogen, oxygen or sulfur atom, such as pyrryl, pyridyl, piperidyl, furyl, tetrahydrofuryl or thienyl, or a group, preferably a monocyclic group, with two hetero atoms selected from nitrogen, oxygen and sulfur, such as imidazolyl, pyrimidinyl, piperazinyl, oxazolyl, isoxazolyl, thiazolyl, morpholinyl or thiomorpholinyl. Preferably, heterocyclic is a monocyclic group having 5- or 6-ring atoms and one or two nitrogen atoms, or one nitrogen atom and one oxygen atom, in the ring and optionally substituted on a ring nitrogen atom by $C_1$-$C_4$alkyl, hydroxy$C_1$-$C_4$alkyl, $C_1$-$C_4$alkylcarbonyl or phenyl$C_1$-$C_4$alkyl.

"Heteroaralkyl" means straight-chain or branched-aralkyl, e.g., one of the $C_6$-$C_{10}$aryl$C_1$-$C_{10}$alkyl groups mentioned hereinbefore, substituted by one or more heterocyclic groups.

"Haloalkyl" means straight-chain or branched-alkyl, e.g., $C_1$-$C_{10}$alkyl, such as one of the $C_1$-$C_{10}$alkyl groups mentioned hereinbefore, substituted by one or more, e.g., one, two or three, halogen atoms, preferably fluorine or chlorine atoms. Preferably haloalkyl is $C_1$-$C_4$alkyl substituted by one, two or three fluorine or chlorine atoms.

"Substituted silyl group" is preferably a silyl group substituted with at least one alkyl group as herein defined.

In a second aspect the invention provides a process for preparing 5-[(R)-2-(5,6-diethyl-indan-2-ylamino)-1-hydroxy-ethyl]-8-hydroxy-(1H)-quinolin-2-one salt or an acceptable solvate thereof comprising:

(a) reacting an 8-(substituted oxy)-5-haloacetyl-(1H)-quinolin-2-one with a reducing agent in the presence of a chiral catalyst to form 8-(substituted oxy)-5-((R)-2-halo-1-hydroxy-ethyl)-(1H)-quinolin-2-one;

(b) treating the 8-(substituted oxy)-5-((R)-2-halo-1-hydroxy-ethyl)-(1H)-quinolin-2-one with a base in the presence of a solvent to form 8-(substituted oxy)-5-(R)-oxiranyl-(1H)-quinolin-2-one;

(c) reacting the 8-substituted oxy-5-(R)-oxiranyl-(1H)-quinolin-2-one having Formula (I)

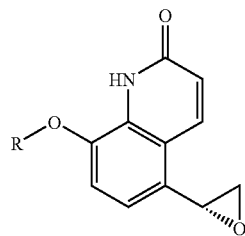

with 2-amino-(5-6-diethyl)-indan to form a reaction mixture containing compounds having Formulae (II), (III) and (IV)

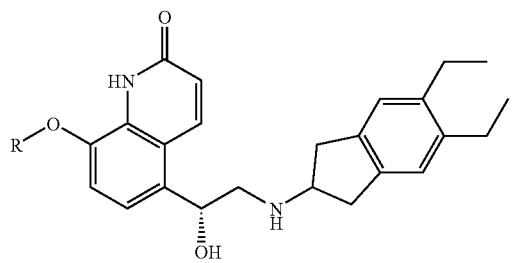

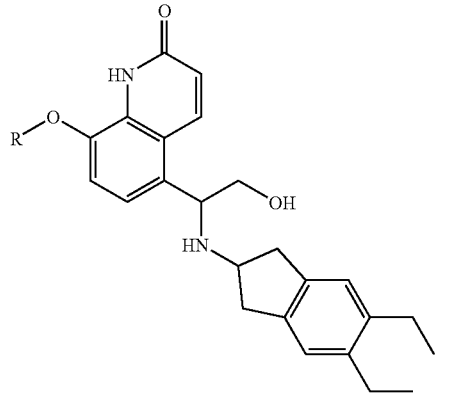

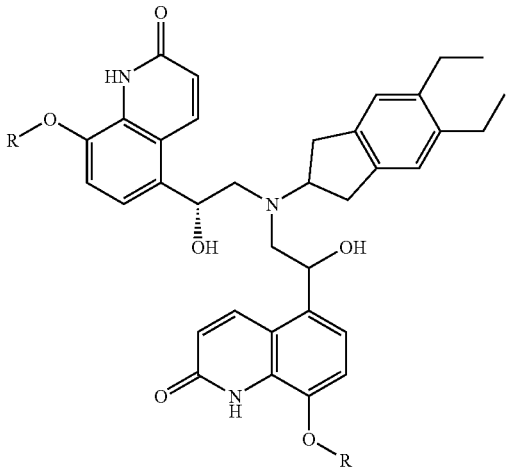

wherein R is a protecting group;

(d) treating the reaction mixture prepared in Step (i) with an acid in the presence of a solvent to form a corresponding salt;

(e) isolating and crystallizing a salt having Formula (V)

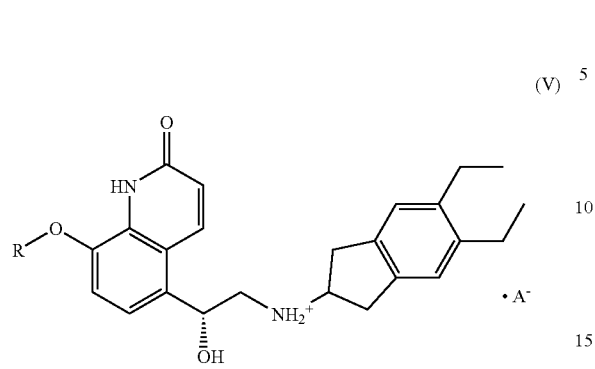

wherein R is a protecting group and A- is an anion;

(f) removing the protecting group from the salt having Formula (V) in the presence of a solvent to form a salt having Formula (VI):

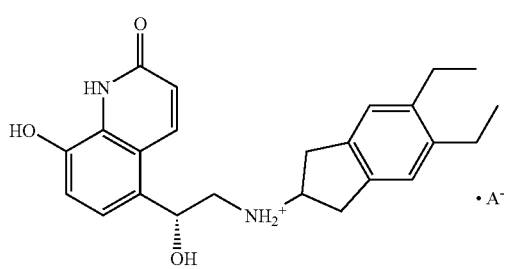

wherein A- is an anion; and (g) treating the salt having Formula (VI) with an acid in the presence of a solvent to form 5-[(R)-2-(5,6-diethyl-indan-2-ylamino)-1-hydroxy-ethyl]-8-hydroxy-(1H)-quinolin-2-one salt having Formula (VII)

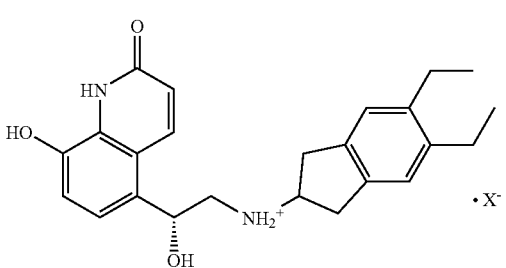

wherein X— is an anion.

The present invention provides a process for preparing 5-[(R)-2-(5,6-diethyl-indan-2-ylamino)-1-hydroxy-ethyl]-8-hydroxy-(1H)-quinolin-2-one salt or an acceptable solvate thereof.

In the first step, Step (i), 8-substituted oxy-5-(R)-oxiranyl-(1H)-quinolin-2-one having Formula (I)

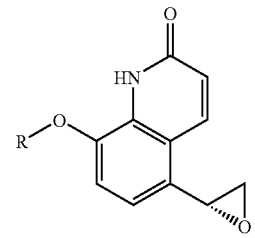

is reacted with 2-amino-(5-6-diethyl)-indan to form a reaction mixture containing compounds having Formulae (II), (III) and (IV):

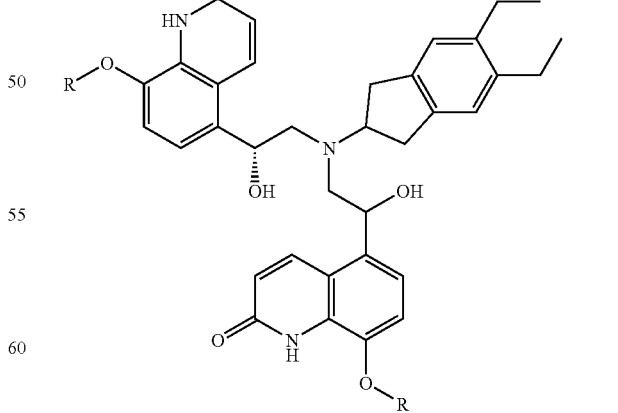

wherein R is a protecting group.

Preferred protecting groups are phenol protecting groups which are known to those skilled in the art. More preferably, the protecting group is selected from the group consisting of an alkyl, aryl, alkoxy, alkenyl, cycloalkyl, benzocycloalkyl, cycloalkylalkyl, aralkyl, heterocyclic, heteroaralkyl, haloalkyl, and a substituted silyl group. Most preferably, the protecting group is benzyl or t-butyldimethylsilyl.

Preferably, Step (i) is conducted in the presence of a solvent. Preferred solvents include: alcohols, e.g., $C_{1-6}$alkyl alcohols, such as methanol, ethanol, propanol, butanol, and pentanol; aliphatic $C_{6-12}$hydrocarbons, e.g., isooctane, heptane;dimethylformamide; aromatic hydrocarbons, such as toluene and benzene; acetonitrile; heterocycles, such as tetrahydrofuran; dialkyl ethers, e.g., diisopropyl ether, 2-methoxyethyl ether and diethylene ether; dimethyl sulfoxide; tetrahydrothiophene 1,1-dioxide, also known as tetramethylene sulfone or as tetramethylene sulfolane; dialkyl carbonate, e.g., dimethyl carbonate and diethyl carbonate; aqueous solvents, such as water; ionic liquids; and chlorinated solvents, such as methylenechloride. A combination of solvents may also be used. More preferably, the solvent is 2-methoxyethyl ether or butanol.

The temperature used in Step (i) is preferably from about 10° C. to about 160° C. More preferably, the temperature is from about 30° C. to about 120° C.; and most preferably from about 90° C. to about 120° C.

Preferably, Step (i) is conducted with a molar excess of the 2-amino-(5-6-diethyl)-indan with respect to the 8-substituted oxy-5-(R)-oxiranyl-(1H)-quinolin-2-one. Preferably, 1.05 mole equivalent to 3 mole equivalents of 2-amino-(5-6-diethyl)-indan is used with respect to 8-substituted oxy-5-(R)-oxiranyl-(1H)-quinolin-2-one. Most preferably, 1.1 mole equivalents to 1.5 mole equivalents of 2-amino-(5-6-diethyl)-indan is used with respect to 8-substituted oxy-5-(R)-oxiranyl-(1H)-quinolin-2-one.

The 8-substituted oxy-5-(R)-oxiranyl-(1H-quinolin-2-one is preferably 8-phenylmethoxy-5-(R)-oxiranyl-(1H)-quinolin-2-one. The 5-[(R)-2-(5,6-diethyl-indan-2-ylamino)-1-hydroxy-ethyl]-8-substituted oxy-(1H)-quinolin-2-one is preferably 5- [(R)-2-(5,6-diethyl-indan-2-ylamino)-1-hydroxyethyl]-8-phenylmethoxy-(1H)-quinolin-2-one.

The 8-substituted oxy-5-(R)-oxiranyl-(1H)-quinolin-2-one may be prepared by reacting an 8-(substituted oxy)-5-haloacetyl-(1H)-quinolin-2-one with a reducing agent in the presence of a chiral catalyst to form 8-(substituted oxy)-5-((R)-2-halo-1-hydroxy-ethyl)-(1H)-quinolin-2-one; and treating the 8-(substituted oxy)-5-((R)-2-halo-1-hydroxy-ethyl)-(1H)-quinolin-2-one with a base in the presence of a solvent to form 8-(substituted oxy)-5-(R)-oxiranyl-(1H)-quinolin-2-one. This is described in greater detail below.

In the second step, Step (ii), the reaction mixture prepared in Step (i) is treated with an acid in the presence of a solvent to form a corresponding salt.

Preferred solvents for use in Step (ii) include: alcohols, e.g., $C_{1-6}$alkyl alcohols, such as methanol, ethanol, propanol, butanol, and pentanol; aliphatic $C_{6-12}$hydrocarbons, e.g., isooctane, heptane; dimethylformamide; aromatic hydrocarbons, such as toluene and benzene; acetonitrile; heterocycles, such as tetrahydrofuran; dialkyl ethers, e.g., diisopropyl ether, 2-methoxyethyl ether and diethylene ether; dimethyl sulfoxide; tetrahydrothiophene 1,1-dioxide, also known as tetramethylene sulfone or as tetramethylene sulfolane; dialkyl carbonate, e.g., dimethyl carbonate and diethyl carbonate; aqueous solvents, such as water; ionic liquids; and chlorinated solvents, such as methylenechloride. A combination of solvents may also be used. More preferably, the solvent is ethanol.

The temperature used in Step (ii) is preferably from about −10° C. to about 160° C. More preferably, the temperature is from about 0° C. to about 120° C.; and most preferably from about 0° C. to about 75° C.

In the third step, Step (iii), a salt having Formula (V)

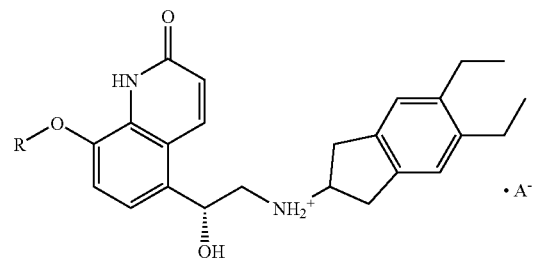

(V)

is isolated and crystallized, wherein R is a protecting group; and A- is an anion. The anion corresponds to the acid used in Step (ii). The acid used in Step (ii) is preferably a carboxylic acid, such as benzoic acid, maleic acid, succinic acid, fumaric acid, or tartaric acid; or a mineral acid, such as hydrochloric acid. Most preferably, the acid used in Step (ii) is benzoic acid.

The salt having Formula (V) is preferably a benzoate salt having Formula (VIII)

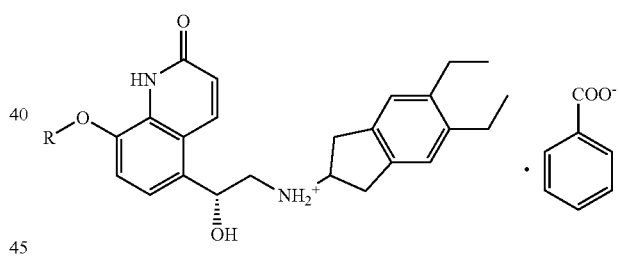

(VIII)

wherein R is a protecting group.

More preferably, the benzoate salt having Formula (VIII) is a benzoate salt having Formula (IX)

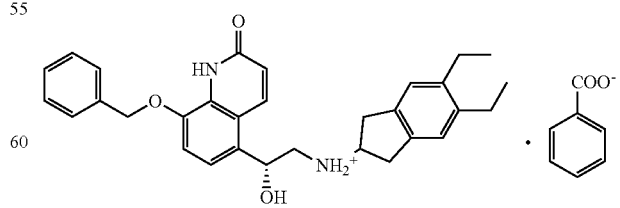

(IX)

In the fourth step, Step (iv), the protecting group on the salt having Formula (V) is removed in the presence of a solvent to form a salt having Formula (VI)

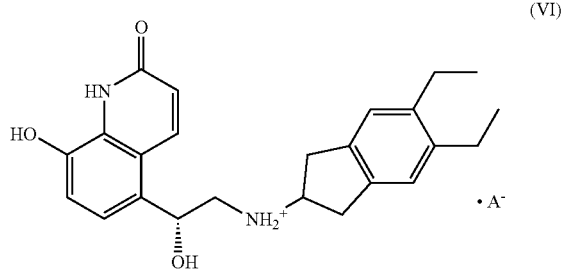

wherein A- is an anion.

The salt having Formula (VI) is preferably a benzoate salt having Formula (X)

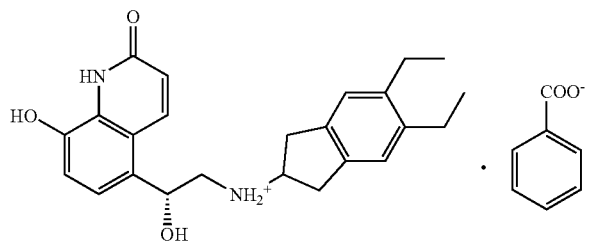

The removal of a protecting group is known to those skilled in the art and depends on the type of protecting group. In one embodiment where the protecting group is benzyl, a preferred method of removing the benzyl group on the salt having Formula (V) is by treating the salt with hydrogen in the presence of a catalyst. Preferred catalysts include palladium, palladium hydroxide, palladium on activated carbon, palladium on alumina, palladium on carbon powder, platinum, platinum on activated carbon and Raneyl™ nickel. A combination of catalysts may also be used. Most preferably, the catalyst is palladium on activated carbon.

In one embodiment where the protecting group is t-butyldimethylsilyl, a preferred method of removing the t-butyldimethylsilyl group on the salt having Formula (V) is by treating the salt with t-butylammonium fluoride or potassium fluoride.

The solvent used in Step (iv) is preferably selected from an alkyl acetate, e.g., $C_{1-6}$alkyl acetates, such as ethyl acetate, isopropyl acetate and butyl acetate; lower alkyl alkylamines, e.g., $C_{1-6}$alkylamines; alcohols, e.g., $C_{1-6}$alkyl alcohols, such as methanol, ethanol, propanol, butanol and pentanol; aliphatic $C_{6-12}$hydrocarbons, e.g., isooctane, heptane, dimethylformamide; aromatic hydrocarbons, such as toluene and benzene; acetonitrile; heterocycles, such as tetrahydrofuran; dialkyl ethers, e.g., diisopropyl ether, 2-methoxyethyl ether, and diethylene ether; an acid, e.g., acetic acid, trifluoroacetic acid, and propionic acid; aqueous solvents, such as water; ionic liquids; and chlorinated solvents, such as methylenechloride. A combination of solvents may also be used. More preferably, the solvent is acetic acid or 2-propanol.

The temperature used in Step (iv) is preferably from about 0° C. to about 70° C. More preferably, the temperature is from about 10° C. to about 50° C.; and most preferably from about 10° C. to about 30° C.

The salt having Formula (VI) is preferably 5-[(R)-2-(5,6-diethyl-indan-2-ylamino)-1-hydroxy -ethyl]-8-hydroxy-(1H)-quinolin-2-one benzoate.

In the fifth step, Step (v), the salt having Formula (VI) is treated with an acid in the presence of a solvent to form a salt having Formula (VII)

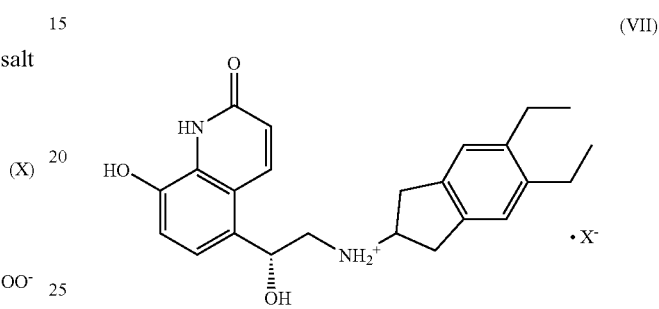

wherein X— is an anion. The anion corresponds to the acid used in Step (v). The acid used in Step (v) is preferably a carboxylic acid, such as benzoic acid, maleic acid, succinic acid, fumaric acid, or tartaric acid. Most preferably, the acid used in Step (v) is maleic acid.

The salt having Formula (VII) is isolated, preferably by filtration. The salt having Formula (VII) is preferably 5-[(R)-2-(5,6-diethyl-indan-2-ylamino)-1-hydroxy-ethyl]-8-hydroxy-(1H)-quinolin-2-one maleate having Formula (XI):

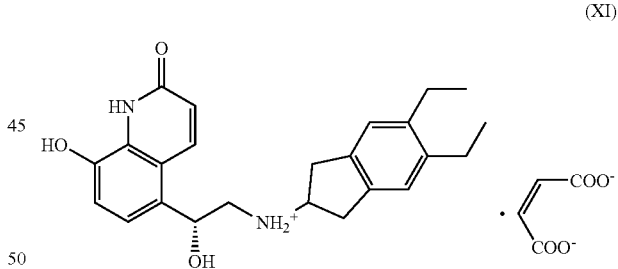

The solvent used in Step (v) is preferably selected from an alkyl acetate, e.g., $C_{1-6}$alkyl acetates, such as ethyl acetate, isopropyl acetate and butyl acetate; alcohols, e.g., $C_{1-6}$alkyl alcohols, such as methanol, ethanol, propanol, isopropanol, butanol and pentanol; dimethylformamide; aromatic hydrocarbons, such as toluene and benzene; dialkyl ketones, e.g., acetone and methyl isobutyl ketone; acetonitrile; heterocycles, such as tetrahydrofuran; dialkyl ethers, e.g., diisopropyl ether, 2-methoxyethyl ether and diethylene ether; an acid such as acetic acid and propionic acid; aqueous solvents, such as water; ionic liquids; and chlorinated solvents, such as methylenechloride. A combination of solvents may also be used. More preferably, the solvent is ethanol.

The temperature used in Step (v) is preferably from about 0° C. to about 70° C. More preferably, the temperature is from about 10° C. to about 60° C.; and most preferably from about 20° C. to about 50° C.

As mentioned above, the 8-substituted oxy-5-(R)-oxiranyl-(1H)-quinolin-2-one may be prepared by (a) reacting an 8-(substituted oxy)-5-haloacetyl-(1H)-quinolin-2-one with a reducing agent in the presence of a chiral catalyst to form 8-(substituted oxy)-5-((R)-2-halo-1-hydroxy-ethyl)-(1H)-quinolin-2-one; and then (b) treating the 8-(substituted oxy)-5-((R)-2-halo-1-hydroxy-ethyl)-(1H)-quinolin-2-one with a base in the presence of a solvent to form 8-(substituted oxy)-5-(R)-oxiranyl-(1H)-quinolin-2-one.

For example, in Step (a), the 8-substituted oxy-5-haloacetyl-(1H)-quinolin-2-one is reacted with a reducing agent in the presence of a chiral catalyst to form a 8-substituted oxy-5-((R)-2-halo-1-hydroxy-ethyl)-(1H)-quinolin-2-one of Formula (XII):

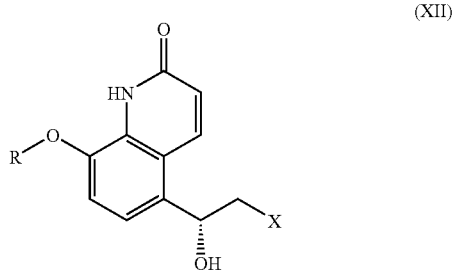

(XII)

wherein R is a protecting group; and X is a halogen. The halogen is selected from bromine, chlorine, fluorine and iodine. Preferably, the halogen is chlorine.

The 8-substituted oxy-5-haloacetyl-(1H)-quinolin-2-one is commercially available or may be prepared by halogenating the corresponding methylketone, for example using the procedure described in international patent application WO 95/25104. The methylketone is commercially available or may be prepared using the procedure described in *European Journal of Medicinal Chemistry*, 1984, 19, 341-346.

Preferably, the chiral catalyst is an oxazaborolidine compound of Formula (XIII):

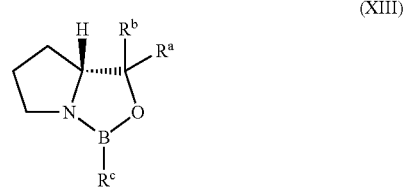

(XIII)

wherein $R^a$ and $R^b$ are, independently, selected from an aliphatic, cycloaliphatic, cycloaliphatic-aliphatic, aryl or aryl-aliphatic residue. Preferably, $R^a$ and $R^b$ are, independently, selected from phenyl, 4-methylphenyl, and 3,5-dimethylphenyl. More preferably, $R^a$ and $R^b$ are phenyl, and $R^c$ is selected from aliphatic, cycloaliphatic, cycloaliphatic-aliphatic, aryl or aryl-aliphatic residue, which, in each case, may be linked to a polymer. More preferably, $R^c$ is methyl.

$R^a$, $R^b$ and $R^c$ are preferably unsubstituted but may be substituted, example, by one or more, e.g., two or three, residues, e.g., those selected from $C_1$-$C_7$ alkyl, hydroxy, —O—CH$_2$—O—, —CHO, $C_1$-$C_7$ substituted oxy, $C_2$-$C_8$ alkanoyl-oxy, halogen, e.g., chlorine or fluorine, nitro, cyano and $CF_3$.

Aliphatic hydrocarbon residues include $C_1$-$C_7$ alkyl, $C_2$-$C_7$ alkenyl or secondarily $C_2$-$C_7$ alkynyl. $C_2$-$C_7$ Alkenyl is, in particular, $C_3$-$C_7$ alkenyl and is, e.g., 2-propenyl or 1-, 2- or 3-butenyl. $C_3$-$C_5$ Alkenyl is preferred. $C_2$-$C_7$ Alkynyl is, in particular, $C_3$-$C_7$ alkynyl and is preferably propylnyl.

Cycloaliphatic residues include $C_3$-$C_8$ cycloalkyl or, secondarily, $C_3$-$C_8$ cycloalkenyl. $C_3$-$C_8$ cycloalkyl is preferably cyclopentyl or cyclohexyl. $C_3$-$C_8$ Cycloalkenyl is $C_3$-$C_7$ cycloalkenyl is preferably cyclopent-2-en-yl and cyclopent-3-enyl, or cyclohex-2-en-yl and cyclohex-3-en-yl.

Cycloaliphatic-aliphatic residues include $C_3$-$C_8$ cycloalkyl-$C_1$-$C_7$ alkyl, preferably $C_3$-$C_6$ cycloalkyl-$C_1$-$C_4$ alkyl, but especially cyclopropylmethyl.

The aryl residue may be, for example, a carbocyclic or heterocyclic aromatic residue, in particular, phenyl or, in particular, an appropriate 5- or 6-membered and mono or multicyclic residue which has up to four identical or different hetero atoms, such as nitrogen, oxygen or sulfur atoms, preferably one, two, three or four nitrogen atoms, an oxygen atom or a sulfur atom. Suitable 5-membered heteroaryl residues include monoaza-, diaza-, triaza-, tetraaza-, monooxa- or monothia-cyclic aryl radicals, such as pyrrolyl, pyrazolyl, imidazolyl, triazolyl, tetrazolyl, furyl and thienyl, while suitable appropriate 6-membered residues are, in particular, pyridyl. Appropriate multicyclic residues are anthracenyl, phenanthryl, benzo[1,3]-dioxole or pyrenyl. An aryl residue may be mono-substituted by, e.g., $NH_2$, OH, $SO_3H$, CHO or di-substituted by OH or CHO and $SO_3H$.

Aryl-aliphatic residues include phenyl-$C_1$-$C_7$ alkyl, phenyl-$C_2$-$C_7$ alkenyl and phenyl-$C_2$-$C_7$ alkynyl.

Suitable polymers include polystyrene (PS), cross-linked PS (J), polyethylene glycol (PEG) or a silica gel residue (Si). Examples are NH—$R^d$, wherein $R^d$ is $C(O)(CH_2)_n$—PS or $C(O)NH(CH_2)_n$—PS; and —O—Si($R^e$)$_2$(CH$_2$)$_n$$R^f$, wherein n is 1-7, $R^e$ is $C_1$-$C_6$ alkyl, e.g., ethyl, and $R^f$ is a polystyrene, cross-linked polystryrene, polyethylene glycol or a silica gel residue.

The reducing agent that is used to reduce the 8-(substituted oxy)-5-haloacetyl-(1H)-quinolin-2-one is preferably a borane reagent such as borane-tetrahydrofuran complex, a borane-N,N-diethylaniline complex or a borane-methyl sulfide complex. A borane-tetrahydrofuran complex is especially preferred. The oxazaborolidine chiral catalyst is preferably (R)-tetrahydro-1-methyl-3,3-diphenyl-(1H,3H)-pyrrolo[1,2-c][1,3,2]-oxazaborole, also known as (R)-2-methyl-CBS-oxazaborolidine (Me-CBS).

Preferably a solvent is used in Step (a). Preferred solvents include: an alkyl acetate, e.g., $C_{1-6}$ alkyl acetates, such as ethyl acetate, isopropyl acetate and butyl acetate; alkylamines, e.g., $C_{1-6}$alkylamines; lower alkyl alcohols, e.g., $C_{1-6}$alkyl alcohols, such as methanol, ethanol, propanol, isopropanol, butanol, and pentanol; aliphatic $C_{6-12}$ hydrocarbons, e.g., isooctane, heptane; dimethylformamide; aromatic hydrocarbons, such as toluene and benzene; acetonitrile; heterocycles, such as tetrahydrofuran; dialkyl ethers, e.g., diisopropyl ether, 2-methoxyethyl ether, and diethylene ether; aqueous solvents, such as water; ionic liquids; and chlorinated solvents, such as methylenechloride. A combination of solvents may also be used. The preferred solvent for use in Step (a) is tetrahydrofuran.

The temperature used in Step (a) is preferably from about −10° C. to about 80° C. More preferably, the temperature is from about 0° C. to about 50° C.

The 8-substituted oxy-5-((R)-2-halo-1-hydroxy-ethyl)-(1H)-quinolin-2-one is preferably 8-phenylmethoxy-5-((R)-2-chloro-1-hydroxy-ethyl)-(1H)-quinolin-2-one.

Optionally, the 8-substituted oxy-5-((R)-2-halo-1-hydroxy-ethyl)-(1H)-quinolin-2-one product may be purified by any of the various techniques known to the art, such as by crystallization, and may, optionally, be conducted in the presence of charcoal.

In the Step (b), the 8-substituted oxy-5-((R)-2-halo-1-hydroxy-ethyl)-(1H)-quinolin-2-one is treated with a base in the presence of a solvent to form 8-substituted oxy-5-(R)-oxiranyl-(1H)-quinolin-2-one. The 8-substituted oxy-5-(R)-oxiranyl-(1H)-quinolin-2-one has Formula (I):

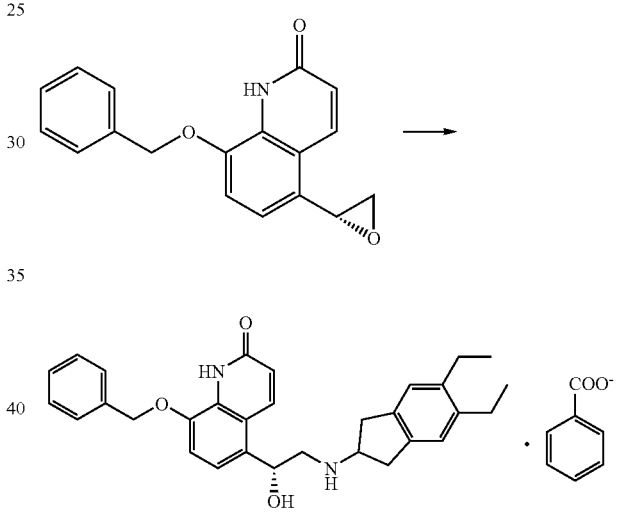

wherein R is a protecting group.

Preferred bases include sodium ethoxide, sodium hydroxide, potassium phosphate, potassium carbonate, potassium hydrogencarbonate and caesium carbonate. A combination of bases may also be used. The base is most preferably potassium carbonate.

The solvent used in Step (b) is preferably selected from an alkyl acetate, e.g., $C_{1-6}$ alkyl acetates, such as ethyl acetate, isopropyl acetate and butyl acetate; alcohols, e.g., $C_{1-6}$alkyl alcohols, such as methanol, ethanol, propanol, butanol, and pentanol; aliphatic $C_{6-12}$ hydrocarbons, e.g., isooctane, heptane; dimethylformamide; aromatic hydrocarbons, such as toluene and benzene; dialkyl ketones, e.g., acetone, methyl isobutyl ketone; acetonitrile; heterocycles, such as tetrahydrofuran; dialkyl ethers, e.g., diisopropyl ether, 2-methoxyethyl ether, and diethylene ether; aqueous solvents, such as water; ionic liquids; and chlorinated solvents such as methylenechloride. A combination of solvents may also be used. A preferred solvent for use in Step (b) is a combination of acetone and water.

The temperature used in Step (b) is preferably from about 10° C. to about 160° C. More preferably, the temperature is from about 30° C. to about 80° C.; and most preferably from about 50° C. to about 60° C.

The 8-substituted oxy-5-(R)-oxiranyl-(1H)-quinolin-2-one is preferably 8-phenlymethoxy-5-(R)-oxiranyl-(1H)-quinolin-2-one.

Optionally, the 8-substituted oxy-5-(R)-oxiranyl-(1H)-quinolin-2-one product may be purified by any of the various techniques known to the art, such as by crystallization.

Crystallization from toluene or acetone is especially preferred, and may, optionally, be conducted in the presence of charcoal.

The invention is illustrated by the following Examples.

EXAMPLE 1

Preparation of 5-[(R)-2-(5,6-diethyl-indan-2-ylamino)-1-hydroxy-ethyl]-8-phenylmethoxy-(1H)-quinolin-2-one benzoate

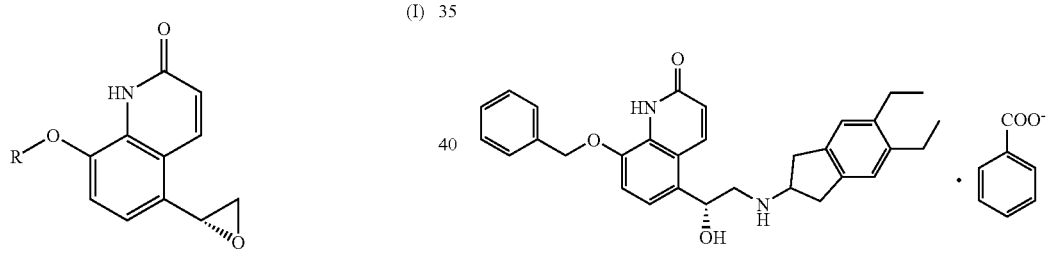

A 1 L, 4-necked flask equipped with a mechanical stirrer, thermometer, addition funnel and refluxing condenser was charged with 30.89 grams of 2-amino-5,6-diethylindan and diethylene glycol dimethyl ether. To this solution was added 36.4 grams of 8-phenylmethoxy-5-(R)-oxiranyl-1H-quinolin-2-one. The resulting suspension was heated to a temperature of 110° C. and stirred at this temperature for 15 hours. The resulting brown solution was cooled to 70° C. At 70° C., 210 mL of ethanol was added followed by a solution of 30.3 grams of benzoic acid in 140 mL of ethanol. The solution was cooled to 45-50° C. and seeded. The suspension was cooled to 0-5° C.

The crude 8-phenylmethoxy-5-[(R)-2-(5,6-diethyl-indan-2-ylamino)-1-hydroxy-ethyl]-1H-quinolin-2-one benzoate was isolated by filtration and washed with 150 mL of ethanol in three portions. The wet filter cake was purified by recrystallization from 1400 mL of ethanol, which gave 50.08 g pure 8-phenylmethoxy-5-[(R)-2-(5,6-diethyl-indan-2-ylamino)-1-hydroxy-ethyl]-1H-quinolin-2-one benzoate as a white crystalline powder.

EXAMPLE 2

Preparation of 5-[(R)-2-(5,6-diethyl-indan-2-ylamino)-1-hydroxy-ethyl]-8-hydroxy-1H-quinolin-2-one maleate

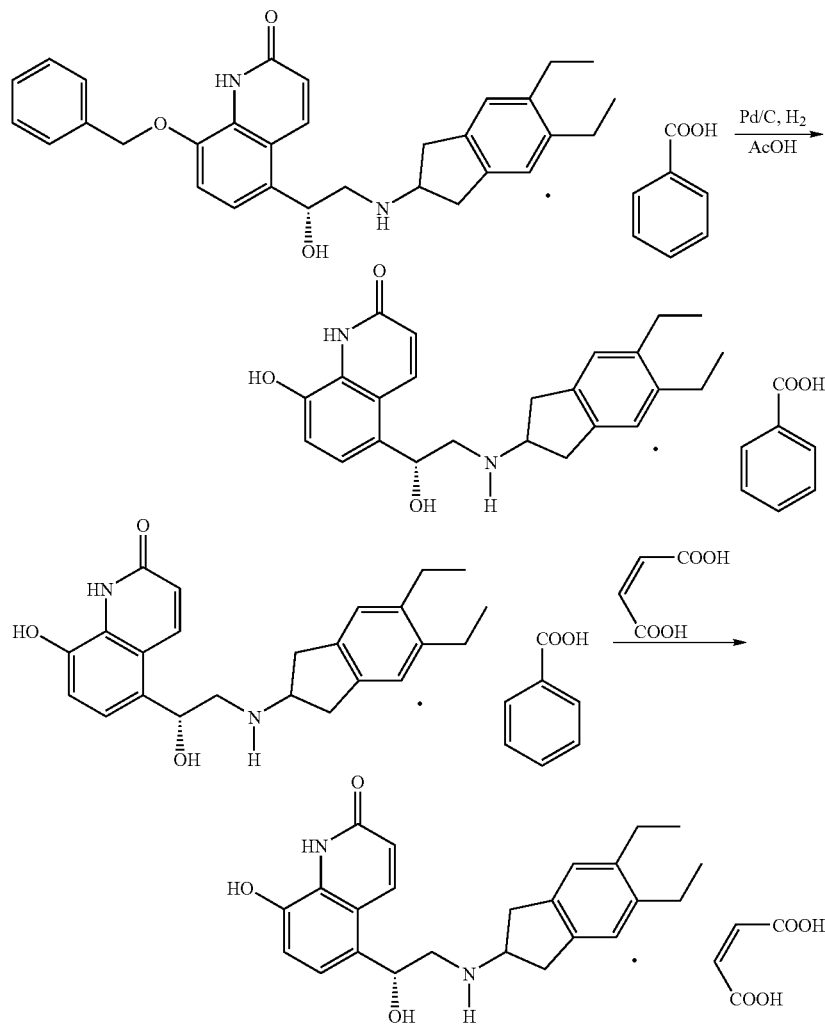

A 1 L hydrogenation vessel was charged with 40 grams of 8-phenylmethloxy-5-[(R)-2-(5,6-diethyl-indan-2-ylamino)-1-hydroxy-ethyl]-1H-quinolin-2-one benzoate and 400 mL of acetic acid. Palladium on charcoal 5% (5.44 g) was added and the reaction mass was hydrogenated for 2-8 hours until complete conversion to 5-[(R)-2-(5,6-diethyl-indan-2-ylamino)-1-hydroxy-ethyl]-8-hydroxy-1H-quinolin-2-one. The mixture was filtered over a pad of filter-aid. The filtrate was concentrated at 50-60° C. under vacuum (100 mbar) to a volume of 70-90 mL. This residue was dissolved in 400 mL of ethanol and heated to 50-60° C. A solution of 11.6 g maleic acid in 24 mL ethanol was added and the resulting clear solution was seeded at an internal temperature of 50° C. with a suspension of 350 mg micronised 5-[(R)-2-(5,6-diethyl-indan-2-ylamino)-1-hydroxy-ethyl]-8-hydroxy-1H-quinolin-2-one in 20 mL isopropanol. The product was crystallized by slow cooling to 0-5° C.

Filtration and washing with 50 mL of ethanol followed by 25 mL of isopropanol provided 65 g crude 5-[(R)-2-(5,6-diethyl-indan-2-ylamino)-1-hydroxy-ethyl]-8-hydroxy-1H-quinolin-2-one maleate which was further purified by crystallization from 1.36 L of ethanol. This gave 24.3 g pure 5-[(R)-2-(5,6-diethyl-indan-2-ylamino)-1-hydroxy-ethyl]-8-hydroxy-1H-quinolin-2-one maleate as a white crystalline powder.

EXAMPLE 3

Purity and Yield of Different Salts of 5-[(R)-2-(5,6-diethyl-indan-2-ylamino)-1-hydroxy-ethyl]-8-substituted oxy-(1H)-quinolin-2-one A 1 L, 4-necked flask equipped with a mechanical stirrer, thermometer, addition funnel and refluxing condenser was charged with 30.89 grams of 2-amino-5,6-diethylindan and diethylene glycol dimethyl ether. To this solution was added 36.4 grams of 8-phenylmethoxy-5-(R)-oxiranyl-1H-quinolin-2-one. The resulting suspension was heated to a temperature of 110° C. and stirred at this temperature for 15 hours. The resulting brown solution was cooled to 70° C.

The reaction was conducted as follows:

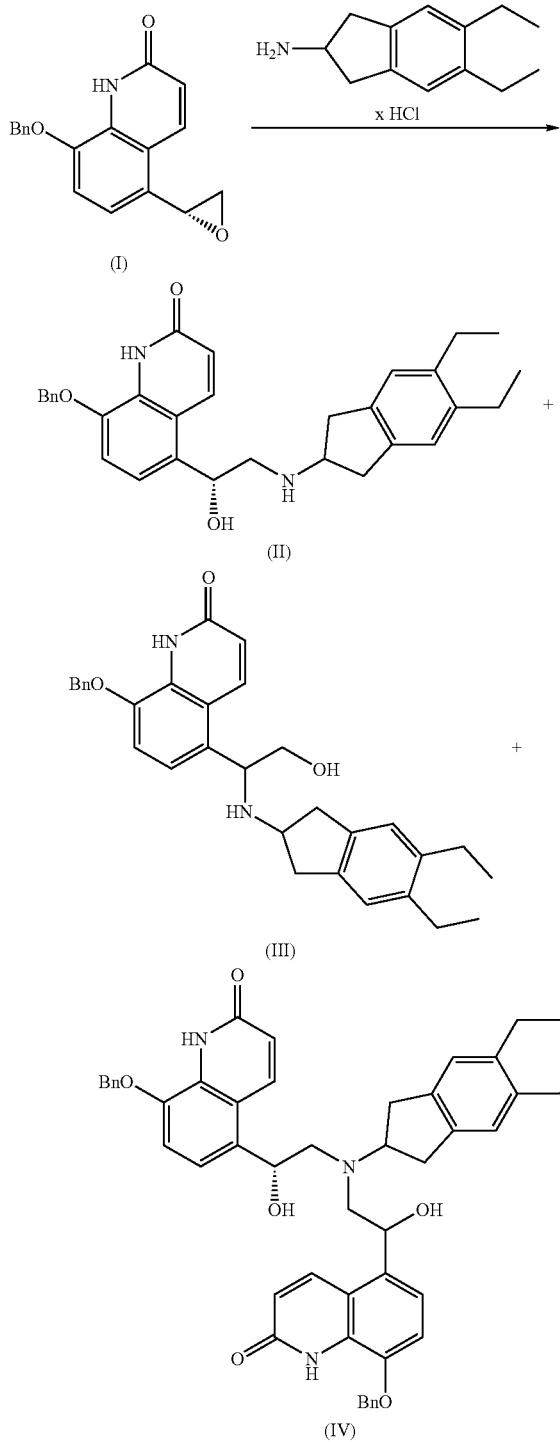

As determined by HPLC, the reaction mixture contained 68.7% of a compound having Formula (II), 7.8% of a compound having Formula (III), and 12.4% of a compound having Formula (IV). The reaction mixture was split in equal portions and each portion was individually treated with an acid selected from benzoic acid, maleic acid, succinic acid, fumaric acid, tartaric acid and hydrochloric acid. The results are summarized in Table 1 as follows:

TABLE 1

| Salt | Purity [%(Area)] | Yield [%] |
|---|---|---|
| Benzoate | 96 | 60 |
| Maleate | 98 | 28 |
| Fumarate | 97 | 48 |
| Succinate | 98 | 30 |
| Tartrate | 98 | 25 |
| Hydrochloride | 87 | 25 |

As set forth in Table 1, the percent yield was based on the amount of 8-substituted oxy-5-(R)-oxiranyl-(1H)-quinolin-2-one, and the purity was based on the salt having Formula (II) and was determined by HPLC.

Thus, it has surprisingly been found that (a) the yield of 5-[(R)-2-(5,6-diethyl-indan-2-ylamino)-1-hydroxy-ethyl]-8-hydroxy-(1H)-quinolin-2-one salt may be significantly increased by forming an acid salt of 5-[(R)-2-(5,6-diethyl-indan-2-ylamino)-1-hydroxy-ethyl]-8-substituted oxy-(1H)-quinolin-2-one; and (b) the acid salt can be converted to a salt of 5-[(R)-2-(5,6-diethyl-indan-2-ylamino)-1-hydroxy-ethyl]-8-hydroxy-(1H)-quinolin-2-one without isolating the free base of 5-[(R)-2-(5,6-diethyl-indan-2-ylamino)-1-hydroxy-ethyl]-8-hydroxy-(1H)-quinolin-2-one.

EXAMPLE 4

Preparation of 8-(phenylmethoxy)-5-((R)-2-chloro-1-hydroxy-ethyl)-(1H)-quinolin-2-one

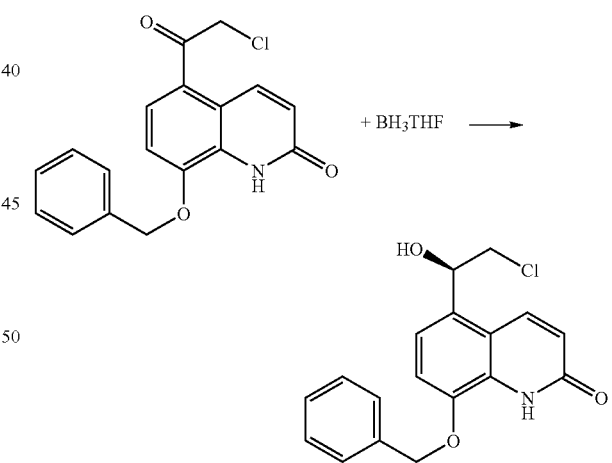

A dry 3 L, 4-necked flask equipped with a mechanical stirrer, thermometer, addition funnel and refluxing condenser is charged with 50 g 8-(phenylmethoxy)-5-(α-chloroacetyl)-(1H)-quinolin-2-one and 600 mL dry THF under $N_2$. Then 15 mL of a 1 molar solution of (R)-tetrahydro-1-methyl-3,3-diphenyl-(1H,3H)-pyrrolo[1,2-c][1,3,2]-oxazaborole in toluene was added. The mixture was cooled to an internal temperature of 0-2° C. and while maintaining an internal temperature of 0-2° C., 153 mL of a 1 molar solution of $BH_3$ in THF was added over 1-2 hours. The reaction was stirred for another hour at an internal temperature of 0-2° C. and then quenched by addition of 65 mL methanol. The resulting solution was warmed to 25° C. and concentrated to a volume of 250 mL (50° C./200 mbar). To this concentrate was added a mixture of 713 mL water and 37 g HCl 37%. During the addition 8-(phenylmethoxy)-5-((R)-2-chloro-1-hydroxy-ethyl)-(1H)-quinolin-2-one precipitated as a nearly colourless precipitation. The resulting suspension was stirred for 30 minutes at 25° C., filtrated and washed with 220 mL water in several portions. Drying in a vacuum drier at 50° C. for 12 hours resulted in 47.41 g of 8-(phenylmethoxy)-5-((R)-2-chloro-1-hydroxy-ethyl)-(1H-quinolin-2-one as a slightly yellowish powder.

EXAMPLE 5

Preparation of 8-(phenylmethoxy)-5-(R)-oxiranyl-(1H)-quinolin-2-one

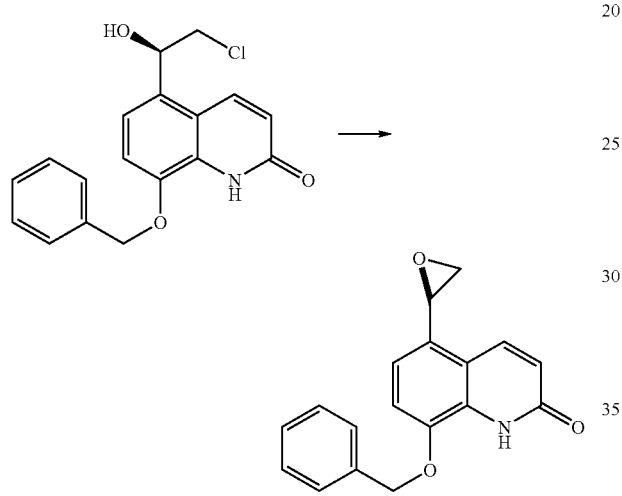

A 3 L, 4-necked flask equipped with a mechanical stirrer, thermometer, addition funnel and refluxing condenser was charged with 50 g 8-(phenylmethoxy)-5-((R)-2-chloro-1-hydroxy-ethyl)-(1H)-quinolin-2-one, 52.42 g potassium carbonate, 2500 mL acetone and 25 mL water. The mixture was heated under stirring to reflux. Refluxing was maintained for 5-10 hours until an in process control showed complete conversion of 8-phenylmethoxy-5-((R)-2-chloro-1-hydroxy-ethyl)-(1H)-quinolin-2-one to 8-phenylmethoxy-5-(R)-oxiranyl-(1H)-quinolin-2-one. When the reaction was completed, the hot (45-50 C) reaction mixture was filtered to remove the inorganic salts. The residue was washed with several portions of acetone, and the combined mother liquor and acetone washings were concentrated to a volume of 450 mL. To the resulting suspension was added 235 mL heptanes at 25° C. and then the suspension was cooled to an internal temperature of 0-2° C. and stirred at this temperature for 2-3 hours. Filtration and washing resulted in a crude 8-phenylmethoxy-5-(R)-oxiranyl-(1H)-quinolin-2-one which was recrystallized from toluene. This resulted in 36.7 g 8-(phenylmethoxy)-5-(R)-oxiranyl-(1H)-quinolin-2-one as nearly colourless solid.

The invention claimed is:
1. A process for preparing 5-[(R)-2-(5,6-diethyl-indan-2-ylamino)-1-hydroxy-ethyl]-8-hydroxy-(1H)-quinolin-2-one salt comprising:

(i) reacting 8-substituted oxy-5-(R)-oxiranyl-(1H)-quinolin-2-one having Formula (I)

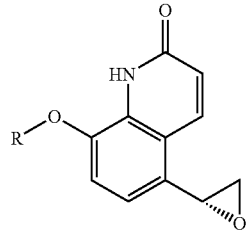

(I)

with 2-amino-(5-6-diethyl)-indan to form a reaction mixture containing compounds having Formulae (II), (III) and (IV)

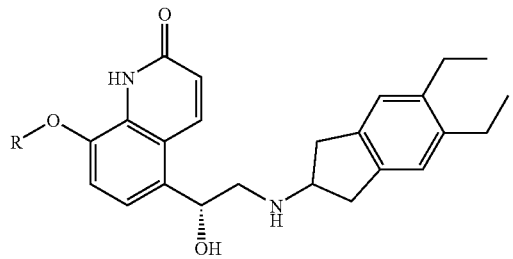

(II)

(III)

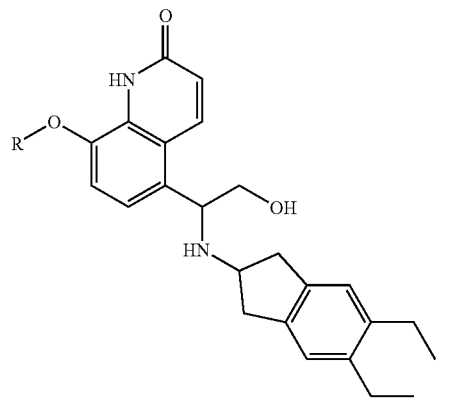

(IV)

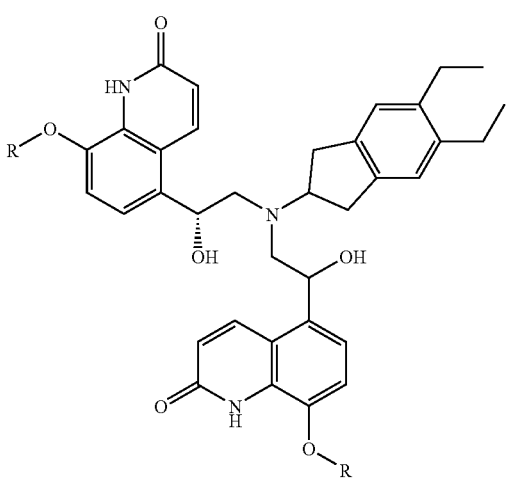

wherein R is a protecting group;

(ii) treating the reaction mixture prepared in Step (i) with an acid in the presence of a solvent to form a corresponding salt;
(iii) isolating and crystallizing a salt having Formula (V)

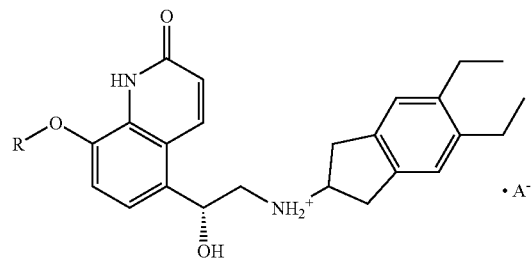

(V)

wherein R is a protecting group and A⁻ is an anion;
(iv) removing the protecting group from the salt having Formula (V) in the presence of a solvent to form a salt having Formula (VI):

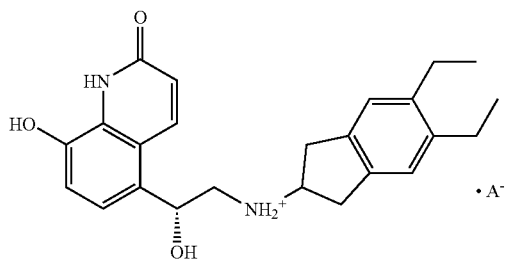

(VI)

wherein A⁻ is an anion; and
(v) treating the salt having Formula (VI) with an acid in the presence of a solvent to form a 5-[(R)-2-(5,6-diethyl-indan-2-ylamino)-1-hydroxy-ethyl]-8-hydroxy-(1H)-quinolin-2-one salt having Formula (VII)

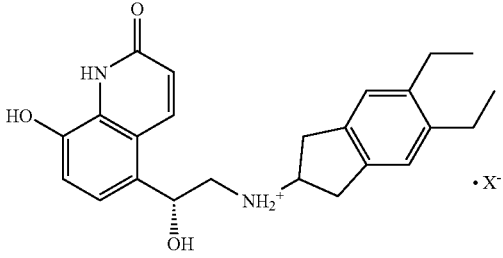

(VII)

wherein X⁻ is an anion.

2. A process for preparing 5-[(R)-2-(5,6-diethyl-indan-2-ylamino)-1-hydroxy-ethyl]-8-hydroxy-(1 H)-quinolin-2-one salt comprising:
(i) reacting 8-substituted oxy-5-(R)-oxiranyl-(1H)-quinolin-2-one having Formula (I)

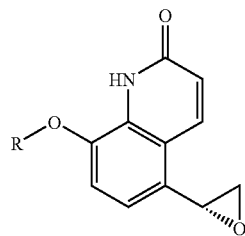

(I)

with 2-amino-(5-6-diethyl)-indan to form a reaction mixture containing compounds having Formulae (II), (III) and (IV)

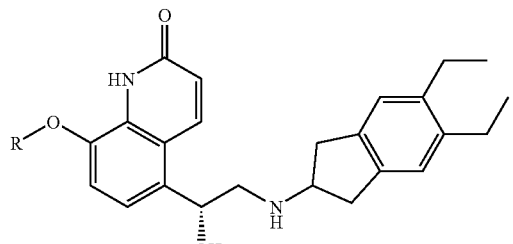

(II)

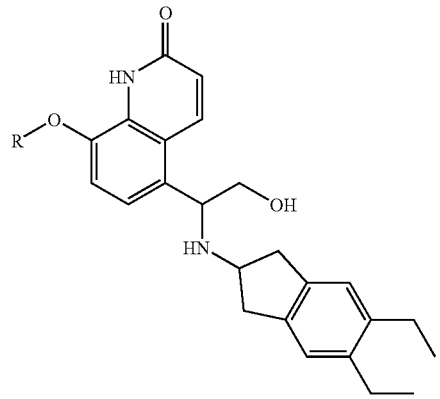

(III)

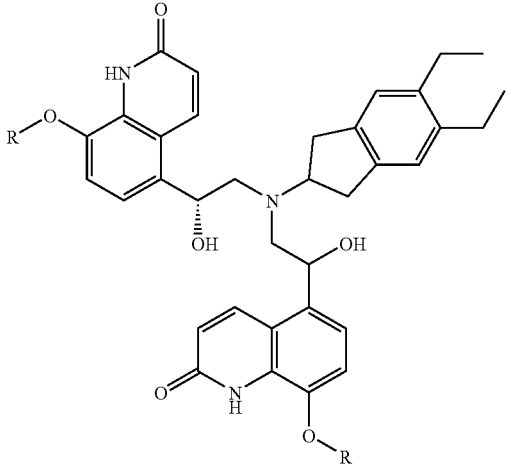

(IV)

wherein R is a protecting group;
(ii) treating the reaction mixture prepared in Step (i) with a carboxylic acid in the presence of a solvent to form a corresponding salt, (iii) isolating and crystallizing a salt having Formula (V)

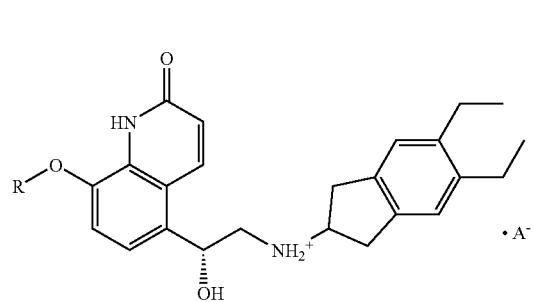

wherein R is a protecting group and A⁻ is an anion;

(iv) removing the protecting group from the salt having Formula (V) in the presence of a solvent to form a salt having Formula (VI):

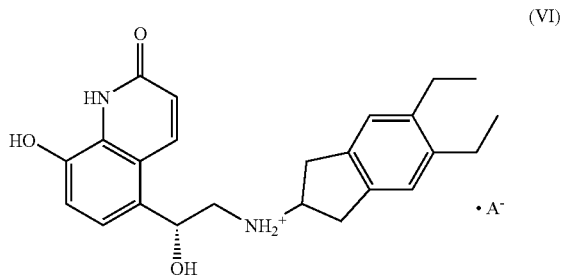

wherein A⁻ is an anion; and (v) treating the salt having Formula (VI) with a carboxylic acid in the presence of a solvent to form a 5-[(R)-2-(5,6-diethyl-indan-2-ylamino)-1-hydroxy-ethyl]-8-hydroxy-(1H)-quinolin-2-one salt having Formula (VII)

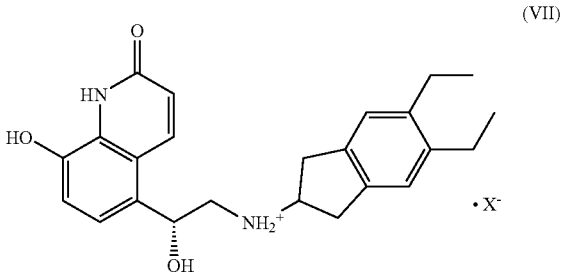

wherein X⁻ is an anion.

3. A process according to claim 2, wherein the carboxylic acid in Step (ii) and or Step (v) is selected from the group consisting of benzoic acid, maleic acid, succinic acid, fumaric acid, and tartaric acid.

4. A process according to claim 3, wherein the carboxylic acid in Step (ii) is benzoic acid.

5. A process according to claim 3, wherein the carboxylic acid in Step (v) is maleic acid.

6. A process according to claim 1, wherein the 5-[(R)-2-(5,6-diethyl-indan-2-ylamino)-1-hydroxy-ethyl]-8-hydroxy-(1H)-quinolin-2-one salt has Formula (XI):

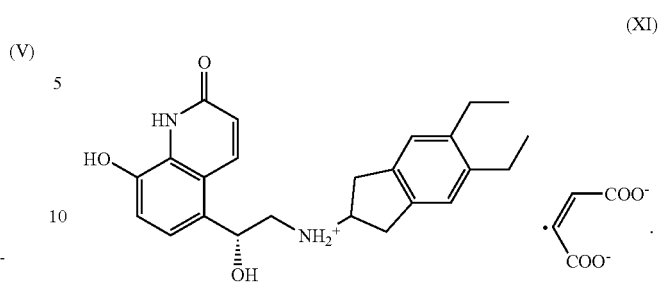

7. A process according to claim 1, wherein the protecting group is selected from the group consisting of an alkyl, aryl, alkoxy, alkenyl, cycloalkyl, benzocycloalkyl, cycloalkylalkyl, aralkyl, heterocyclic, heteroaralkyl, haloalkyl, and a substituted silyl group.

8. A process according to claim 7, wherein the protecting group is benzyl or t-butyldimethylsilyl.

9. A process according to claim 8, wherein the protecting group on the salt having Formula (V) is benzyl and is removed by treating the salt with hydrogen in the presence of a catalyst.

10. A process according to claim 9, wherein the catalyst is selected from the group consisting of palladium, palladium hydroxide, palladium on activated carbon, palladium on alumina, palladium on carbon powder, platinum, platinum on activated carbon, Raney™ nickel and combinations thereof.

11. A process according to claim 8, wherein the protecting group on the salt having Formula (V) is t-butyldimethylsilyl and is removed by treating the salt with t-butylammonium fluoride or potassium fluoride.

12. A process according to claim 1, wherein the temperature in Step (i) is from about 10° C. to about 160° C., the temperature in Step (ii) is from about −10° C. to about 160° C., the temperature in Step (iii) is from about 0° C. to about 70° C., the temperature in Step (iv) is from about 0° C. to about 70° C., and the temperature in Step (v) is from about 0° C. to about 70° C.

13. A process according to claim 1, wherein in Step (i) a molar excess of 2-amino-(5-6-diethyl)-indan is used based on the amount of 8-substituted oxy-5-(R)-oxiranyl-(1H)-quinolin-2-one.

14. A process according to claim 1, wherein the salt having Formula (V) is 5-[(R)-2-(5,6-diethyl-indan-2-ylamino)-1-hydroxy-ethyl]-8-phenylmethoxy-(1H)-quinolin-2-one benzoate.

15. A process according to claim 1, wherein the 8-substituted oxy-5-(R)-oxiranyl-(1H)-quinolin-2-one of Formula (I) is prepared by the steps comprising:

(a) reacting an 8-(substituted oxy)-5-haloacetyl-(1H)-quinolin-2-one with a reducing agent in the presence of a chiral catalyst to form 8-(substituted oxy)-5-((R)-2-halo-1-hydroxy-ethyl)-(1H)-quinolin-2-one; and (b) treating the 8-(substituted oxy)-5-((R)-2-halo-1-hydroxy-ethyl)-(1H)-quinolin-2-one with a base in the presence of a solvent to form 8-(substituted oxy)-5-(R)-oxiranyl-(1H)-quinolin-2-one.

16. A process according to claim 15 wherein in Step (a) the 8-substituted oxy-5-haloacetyl-(1H)-quinolin-2-one is reacted with a borane reagent in the presence of a oxazaborolidine chiral catalyst.

17. A process according to claim 16 wherein the borane reagent is selected from the group consisting of borane-tetrahydrofuran, borane-N,N-diethylaniline and borane-methyl sulphide, and the chiral catalyst is (R)-tetrahydro-1-methyl-3,3-diphenyl-(1H,3H)-pyrrolo[1,2-c][1,3,2]-oxazaborole.

18. A process according to claim 15 wherein the temperature in Step (a) is from about −10° C. to about 80° C. and the temperature in Step (b) is from about 30° C. to about 80° C.

19. A process for preparing 5-[(R)-2-(5,6-diethyl-indan-2-ylamino)-1-hydroxy-ethyl]-8-hydroxy-(1H)-quinolin-2-one salt or an acceptable solvate thereof comprising:

(a) reacting an 8-(substituted oxy)-5-haloacetyl-(1H)-quinolin-2-one with a reducing agent in the presence of a chiral catalyst to form 8-(substituted oxy)-5-((R)-2-halo-1-hydroxy-ethyl)-(1H)-quinolin-2-one;

(b) treating the 8-(substituted oxy)-5-((R)-2-halo-1-hydroxy-ethyl)-(1H)-quinolin-2-one with a base in the presence of a solvent to form 8-(substituted oxy)-5-(R)-oxiranyl-(1H)-quinolin-2-one;

(c) reacting the 8-substituted oxy-5-(R)-oxiranyl-(1H)-quinolin-2-one having Formula (I)

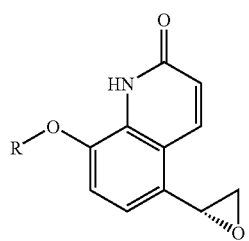
(I)

with 2-amino-(5-6-diethyl)-indan to form a reaction mixture containing compounds having Formulae (II), (III) and (IV)

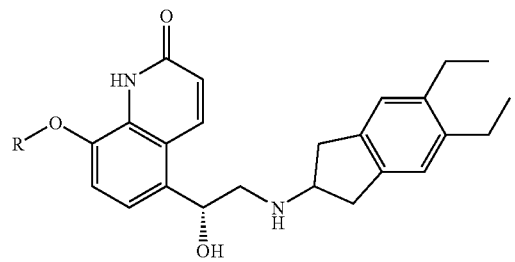
(II)

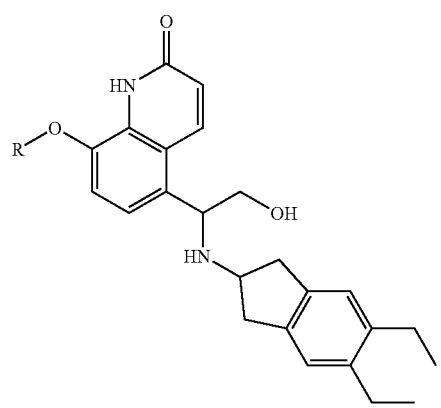
(III)

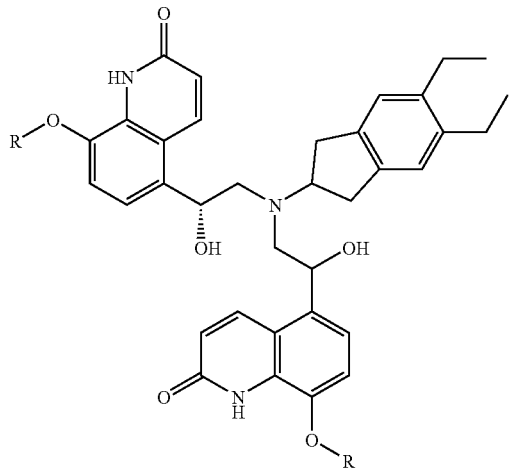
(IV)

wherein R is a protecting group;

(d) treating the reaction mixture prepared in Step (i) with an acid in the presence of a solvent to form a corresponding salt;

(e) isolating and crystallizing a salt having Formula (V)

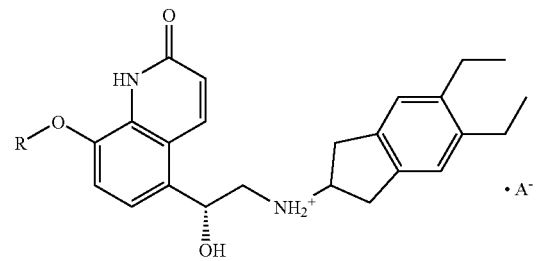
(V)

wherein R is a protecting group and $A^-$ is an anion;

f) removing the protecting group from the salt having Formula (V) in the presence of a solvent to form a salt having Formula (VI):

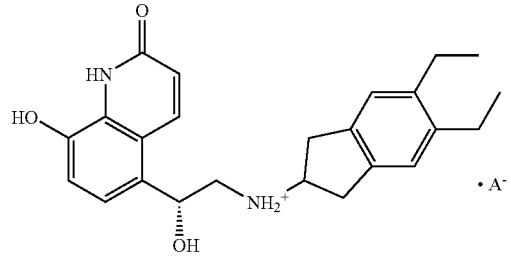
(VI)

wherein $A^-$ is an anion; and (g) treating the salt having Formula (VI) with an acid in the presence of a solvent to form a 5-[(R)-2-(5,6-diethyl-indan-2-ylamino)-1-hydroxy-ethyl]-8-hydroxy-(1H)-quinolin-2-one salt having Formula (VII)

21. A compound having Formula (IX)
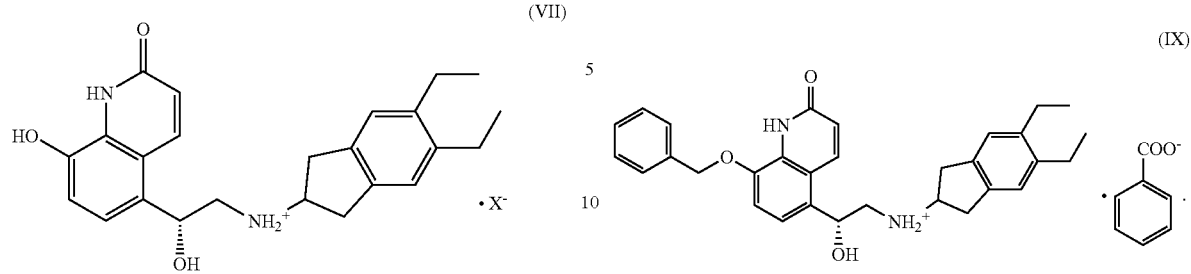
22. A compound having Formula (X)
20. A compound having Formula (VIII)
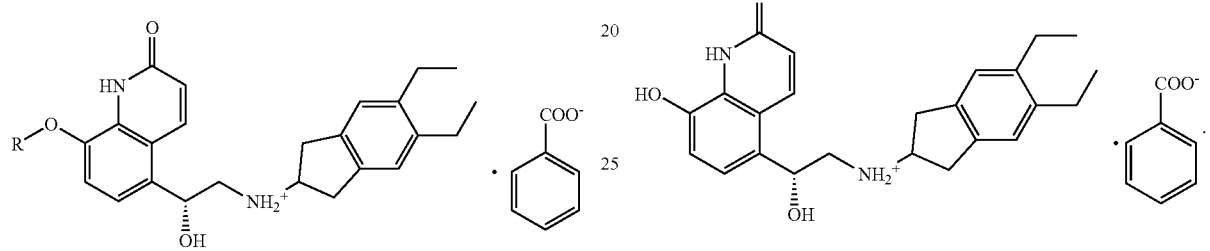
wherein R is a protecting group.
\* \* \* \* \*